(12) United States Patent  
Amagai

(10) Patent No.: US 9,113,841 B2
(45) Date of Patent: Aug. 25, 2015

(54) BIOLOGICAL INFORMATION NOTIFYING APPARATUS, BIOLOGICAL INFORMATION NOTIFYING METHOD, AND COMPUTER-READABLE STORAGE MEDIUM HAVING BIOLOGICAL INFORMATION NOTIFYING PROGRAM STORED THEREON

(71) Applicant: CASIO COMPUTER CO., LTD., Shibuya-ku, Tokyo (JP)

(72) Inventor: Hitoshi Amagai, Hino (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 142 days.

(21) Appl. No.: 14/025,738

(22) Filed: Sep. 12, 2013

(65) Prior Publication Data
US 2014/0077945 A1 Mar. 20, 2014

(30) Foreign Application Priority Data

Sep. 14, 2012 (JP) ................................ 2012-202361

(51) Int. Cl.
*G08B 1/08* (2006.01)
*A61B 5/00* (2006.01)
*A63B 21/00* (2006.01)
*A61B 5/024* (2006.01)

(52) U.S. Cl.
CPC ................. *A61B 5/486* (2013.01); *A63B 21/00* (2013.01); *A61B 5/02438* (2013.01)

(58) Field of Classification Search
None
See application file for complete search history.

(56) References Cited

U.S. PATENT DOCUMENTS

| 6,081,742 A | 6/2000 | Amano et al. |
|---|---|---|
| 2008/0164979 A1* | 7/2008 | Otto .......................... 340/286.01 |
| 2008/0319279 A1 | 12/2008 | Ramsay et al. |

(Continued)

FOREIGN PATENT DOCUMENTS

| CN | 101073496 A | 11/2007 |
|---|---|---|
| JP | 04-269972 A | 9/1992 |
| JP | 2002-240660 A | 8/2002 |

(Continued)

OTHER PUBLICATIONS

Chinese Office Action dated Jan. 12, 2015, issued in counterpart Chinese Application No. 201310418593.9.

(Continued)

*Primary Examiner* — Travis Hunnings
(74) *Attorney, Agent, or Firm* — Holtz, Holtz, Goodman & Chick PC

(57) ABSTRACT

A biological information notifying apparatus of the present invention includes a biological information obtainment sensor to detect biological information of a human body, a vibration section which notifies the biological information by transmitting vibrations to the human body, and a control section which causes the vibration section to vibrate in accordance with the biological information. The control section obtains a first count number of the biological information per a predetermined time period at a first time point, obtains a second count number at a second time point which follows the first time point, causes the vibration section to vibrate with a first vibration in accordance with the biological information, when a difference obtained by subtracting the first count number from the second count number is larger than a positive first value at the second time point.

20 Claims, 14 Drawing Sheets

(56) References Cited

U.S. PATENT DOCUMENTS

2009/0009284 A1    1/2009    Sako
2009/0177097 A1*    7/2009    Ma et al. .................. 600/500

FOREIGN PATENT DOCUMENTS

| | | |
|---|---|---|
| JP | 2004237066 A | 8/2004 |
| JP | 2006-051317 A | 2/2006 |
| JP | 2007-075201 A | 3/2007 |
| JP | 2009015449 A | 1/2009 |
| JP | 2009-142333 A | 7/2009 |
| JP | 2010-530281 A | 9/2010 |
| JP | 2011171954 A | 9/2011 |
| JP | 2012-115373 A | 6/2012 |
| WO | 9810699 A1 | 3/1998 |
| WO | WO 2009/002577 A1 | 12/2008 |

OTHER PUBLICATIONS

Japanese Office Action (and English translation thereof) dated Jun. 23, 2015, issued in counterpart Japanese Application No. 2012-202361.

\* cited by examiner

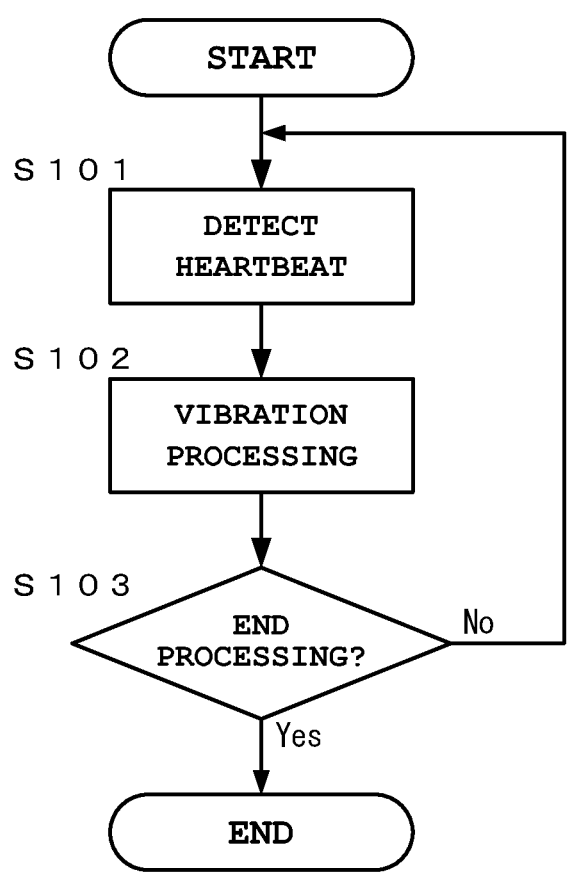

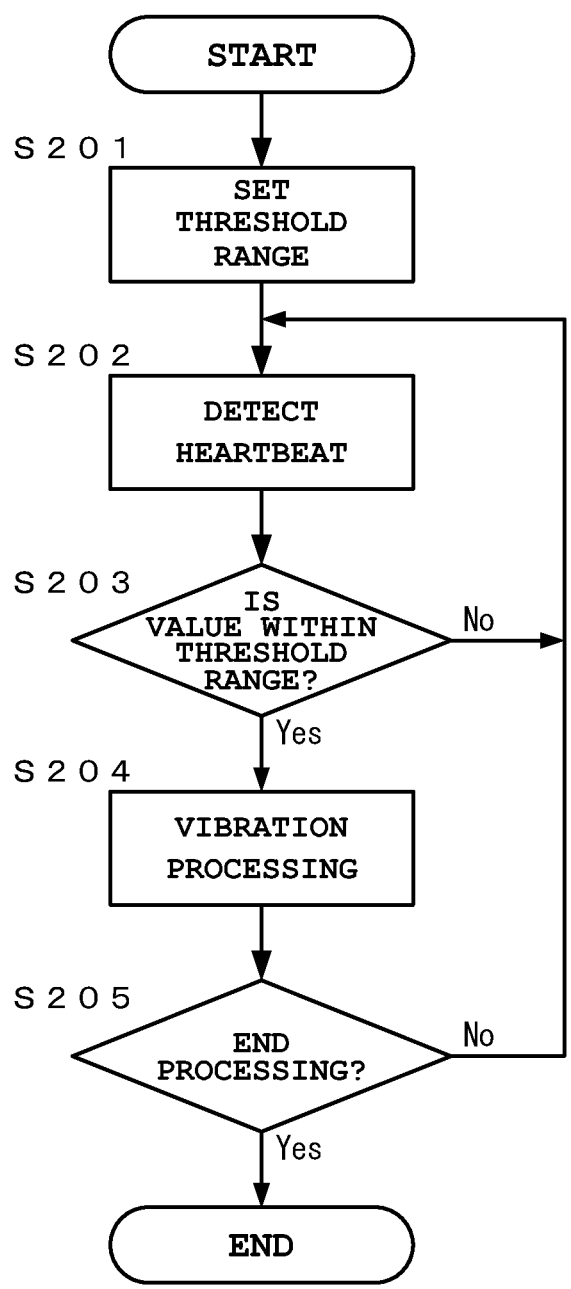

FIG. 11A
FIG. 11B
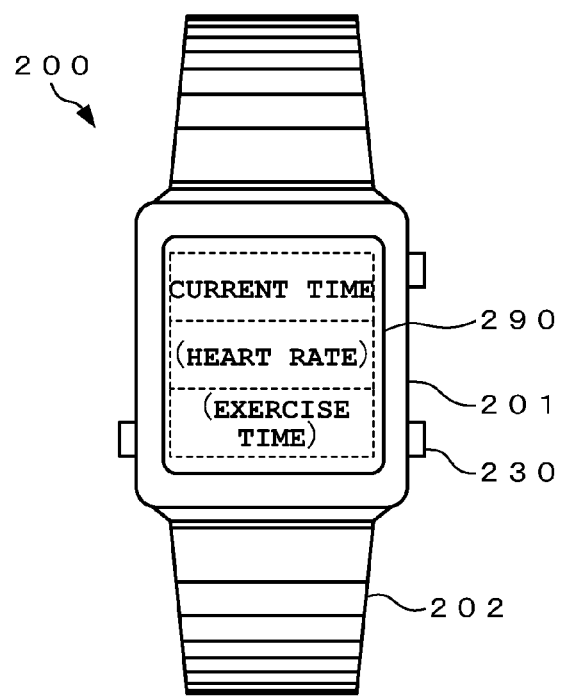

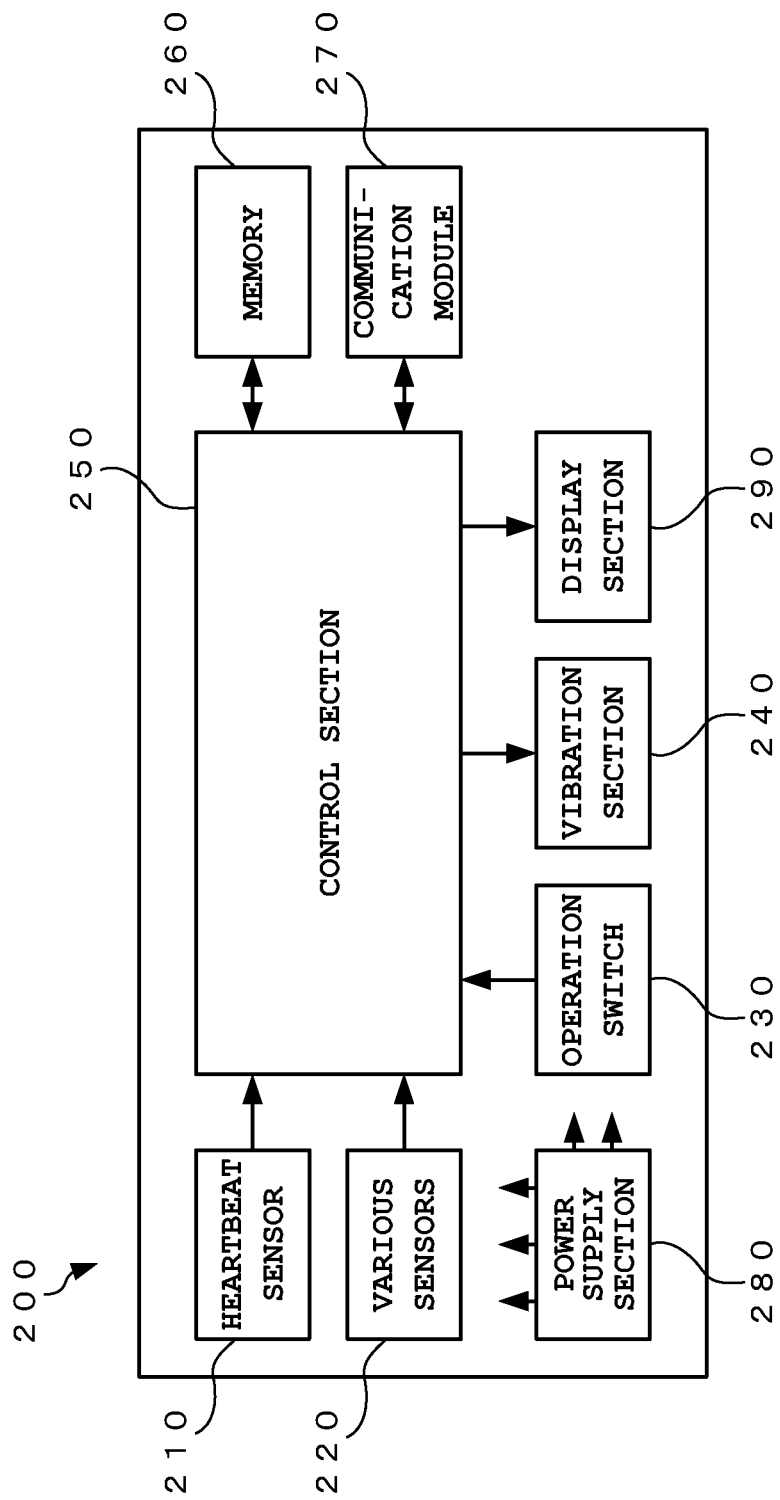

BIOLOGICAL INFORMATION NOTIFYING APPARATUS, BIOLOGICAL INFORMATION NOTIFYING METHOD, AND COMPUTER-READABLE STORAGE MEDIUM HAVING BIOLOGICAL INFORMATION NOTIFYING PROGRAM STORED THEREON

CROSS-REFERENCE TO RELATED APPLICATION

This application is based upon and claims the benefit of priority from the prior Japanese Patent Application No. 2012-202361, filed Sep. 14, 2012, the entire contents of which are incorporated herein by reference.

BACKGROUND OF THE INVENTION

1. Field of the Invention

The present invention relates to a biological information notifying apparatus, a biological information notifying method, and a computer-readable storage medium having a biological information notifying program stored thereon. Specifically, the present invention relates to a biological information notifying apparatus having a biological information measurement function for measuring biological information with the apparatus being mounted on a human body, a biological information notifying method, and a computer-readable storage medium having a biological information notifying program stored thereon.

2. Description of the Related Art

In recent years, because of rising health consciousness, more and more people are performing daily exercises to maintain their wellness or improve their health condition. These people are highly conscious of and interested in measuring and recording their own health condition and exercise condition by using numerical values or data. Currently, various measuring devices supporting this demand are commercially available. By measuring and recording a footstep count, movement distance, pulsation (heart rate), calorie consumption amount, and the like, their own health condition and exercise condition can be grasped.

As an example of this type of measuring device, a heartbeat measuring apparatus has been known which is worn on a wrist or chest part and provides a function for measuring heartbeats, converting the measurement result into numerical values, and displaying the numerical values. For example, Japanese Patent Application Laid-Open (Kokai) Publication No. 2007-075201 discloses a technology in which an apparatus has an outer appearance of a wristwatch that is worn on a wrist and notifies a user of information by sound or display after changing a beep sound generated from notifying means or display of a display section based on whether a heart rate detected by a sensor has exceeded an upper-limit value set in advance. Also, for example, Japanese Patent Application (Kohyo) Publication No. 2010-530281 discloses a technology in which a health condition parameter monitoring apparatus that is worn on a chest part and a tactual feedback generating apparatus that is worn on a wrist are provided and a user is tactually notified of information by vibrations generated by an actuator of the tactual feedback generating apparatus being changed based on whether a heart rate detected by a parameter sensor of the health condition parameter monitoring apparatus or the like has reached a predetermined level.

However, there is a problem in the above-described technologies in that a judgment result regarding whether or not a detected heart rate has exceeded a predetermined set value or level is notified to the user merely by sound and vibrations, and therefore the user cannot accurately grasp a specific heart rate. Also, in a method where a heart rate or the like is displayed on a display section alone or together with the above-described notification by sound and vibrations, it is required to perform a motion of raising an arm or temporarily stop a motion during an exercise in order to visually check the display on the display section during the exercise. However, depending on exercise details (for example, a hard exercise), or the exercise position and the fatigue condition of the user, etc., it may be difficult to perform the above-described motions themselves or quickly read the displayed numerical values, or the motion of checking the display on the display section every time may be bothersome in itself. For example, in a case where the user desires to know in real time how the heart rate changes when attempting to perform various running methods by changing the way of lifting legs, the pitch, the stride, the breathing method, etc., it is very difficult and burdensome to accurately grasp the change while viewing the display on the heartbeat measuring apparatus worn on his or her wrist.

SUMMARY OF THE INVENTION

In accordance with one aspect of the present invention, there is provided a biological information notifying apparatus comprising: a biological information obtainment sensor which detects biological information of a human body; a vibration section which notifies the biological information by transmitting vibrations to the human body; and a control section which causes the vibration section to vibrate in accordance with the biological information, wherein the control section obtains a first count number of the biological information per a predetermined time period at a first time point, and obtains a second count number at a second time point which follows the first time point, and wherein the control section causes the vibration section to vibrate with a first vibration in accordance with the biological information, when a difference obtained by subtracting the first count number from the second count number is larger than a positive first value at the second time point.

In accordance with another aspect of the present invention, there is provided a biological information notifying method comprising: a step of detecting biological information of a human body by a biological information obtainment sensor; a step of obtaining a first count number of the biological information per a predetermined time period at a first time point, and obtaining a second count number at a second time point which follows the first time point; a step of causing a vibration section to vibrate with a first vibration in accordance with the biological information, when a difference obtained by subtracting the first count number from the second count number is larger than a positive first value at the second time point; and a step of notifying the biological information by transmitting the vibration to the human body.

In accordance with another aspect of the present invention, there is provided a non-transitory computer-readable storage medium having stored thereon a program that is executable by a computer, the program being executable by the computer to perform functions comprising: processing for detecting biological information of a human body by a biological information obtainment sensor; processing for obtaining a first count number of the biological information per a predetermined time period at a first time point, and obtaining a second count number at a second time point which follows the first time point; and processing for causing a vibration section to vibrate with a first vibration in accordance with the biological information, when a difference obtained by subtracting the first count number from the second count number is larger than a positive first value at the second time point.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a flowchart of an example of a biological information notifying method for the biological information notifying apparatus according to the first embodiment;

FIG. 5 is a flowchart of an example of a biological information notifying method according to a second embodiment;

FIG. 11A and FIG. 11B are schematic structural diagrams depicting another example of the structure of the biological information notifying apparatus according to the preset invention (first structural example);

FIG. 12 is a functional block diagram of the biological information notifying apparatus according to the first structural example;

DETAILED DESCRIPTION OF THE PREFERRED EMBODIMENTS

A biological information notifying apparatus, a biological information notifying method, and a computer-readable storage medium having a biological information notifying program stored thereon are described in detail below by presenting embodiments.

First Embodiment

Biological Information Notifying Apparatus

Figure 1A:
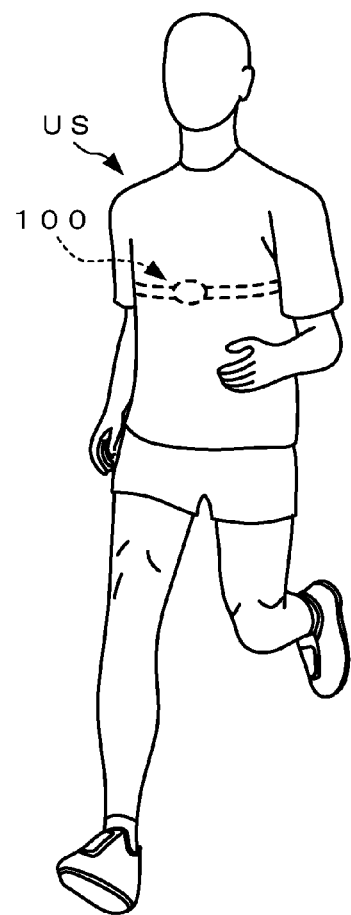
FIG. 1A and FIG. 1B are schematic structural diagrams depicting a first embodiment of a biological information notifying apparatus according to the preset invention.
Figure 1B:
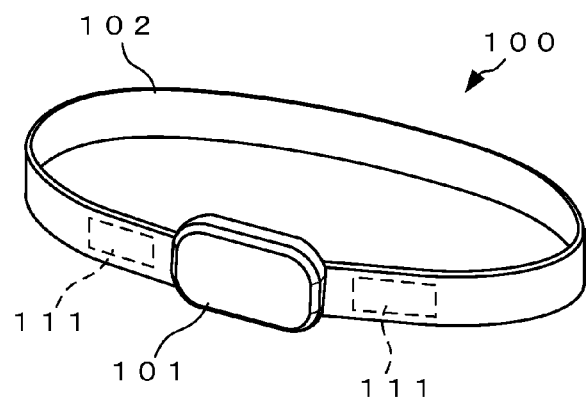
Figure 2:
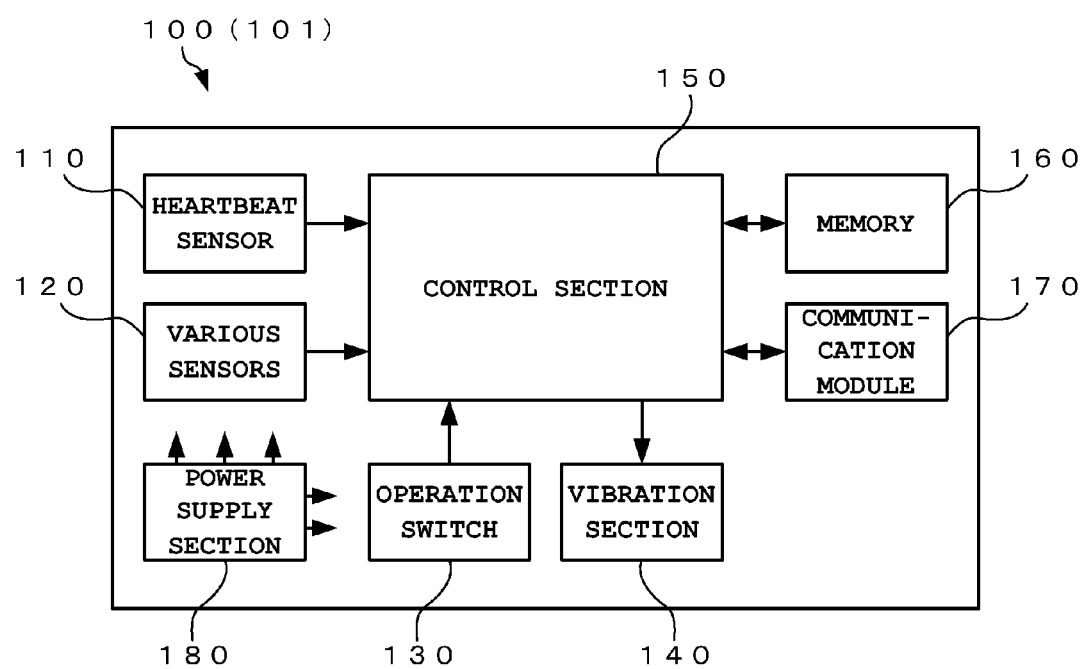
FIG. 2 is a functional block diagram depicting an example of the structure of the biological information notifying apparatus according to the first embodiment.

FIG. 1A and FIG. 1B are schematic structural diagrams depicting a first embodiment of a biological information notifying apparatus according to the preset invention, of which FIG. 1A is a schematic diagram depicting the state where the biological information notifying apparatus according to the present embodiment has been worn on a human body, and FIG. 1B is a schematic structural diagram of an example of the biological information notifying apparatus according to the present embodiment. FIG. 2 is a functional block diagram depicting an example of the structure of the biological information notifying apparatus according to the present embodiment.

The biological information notifying apparatus according to the first embodiment is worn on, for example, the chest part of the user US who is a measurement target, as depicted in FIG. 1A. This biological information notifying apparatus 100 has an outer appearance of a chest sensor as depicted in FIG. 1B, and mainly includes an apparatus main body 101 having a function for detecting various biological information including a heart rate of a user US during an exercise (for example, during walking or running), a belt section 102 that is wound around the chest part of the user US to mount the apparatus main body 101 on the chest part, and paired detection electrodes 111 provided to be exposed to the inner surface side (the side that comes in contact with the human body) of the belt section 102.

Specifically, the apparatus main body 101 includes a heartbeat sensor 110, various sensors 120, an operation switch 130, a vibration section 140, a control section (Central Processing Unit: CPU) 150, a memory 160, a communication module 170, and a power supply section 180, as depicted in FIG. 2.

The heartbeat sensor 110 is exposed to the inner surface side of the belt section 102 for mounting the apparatus main body 101 on the chest part of the user US, and has the paired detection electrodes 111 placed to come in close direct contact with the chest part of the user US, as depicted in FIG. 1B. The heartbeat sensor 110 detects a change of an electrocardiographic signal outputted from the detection electrodes 111, and outputs heartbeat data (sensor data). This heartbeat data is stored in a predetermined storage area of the memory 160.

The sensors 120 are, for example, an acceleration sensor, an angular velocity sensor (gyro sensor), a GPS reception circuit (position sensor), a body temperature sensor, or a respiratory sensor, and detect and output various sensor data associated with exercise status (such as a running speed, a run distance, and a pitch) and those associated with biological status (such as a body temperature, a blood pressure, and a respiratory frequency). These various sensor data are associated with the above-described heartbeat data for each detection time and stored in a predetermined storage area of the memory 160.

Sensors that come in contact with the human body to detect biological information, such as the heartbeat sensor 110, the body temperature sensor, and the respiratory sensor, are collectively referred to as a biological information obtainment sensor.

The operation switch 130 includes a power supply switch and, by the user US operating the operation switch 130, the state of supplying (or cutting) driving electric power from the power supply section 180 to each components in the apparatus main body 101 is controlled to control ON (start) and OFF (stop) of the power supply of the apparatus main body 101. Also, the operation switch 130 includes a sensor control switch and, by the user US operating the operation switch 130, the start or end of a sensing operation in the heartbeat sensor 110 and the various sensors 120 is controlled. Note that a configuration may be adopted in which the operation switch 130 includes only the power supply switch, a sensing operation in the heartbeat sensor 110 and the sensors 120 is started by the user US operating the operation switch 130 to turn on (start) the power supply of the apparatus main body 101, and the sensing operation in the heartbeat sensor 110 and the sensors 120 is ended by the power supply of the apparatus main body 101 being turned off (stopped).

The vibration section 140, which has a vibration device such as a vibration motor or a vibrator, generates vibrations of a predetermined vibration pattern with a predetermined strength (strong or weak) described below in response to at least the heartbeat of the user US detected by the heartbeat sensor 110, and thereby performs an operation of tactually notifying the user US of heartbeat information.

The memory 160 has a non-volatile memory, and stores heartbeat data outputted from the heartbeat sensor 110 and various sensor data associated with a exercise status and a biological status outputted from the various sensors 120 in association with each other in a predetermined storage area for each detection time. The memory 160 also temporarily stores various data to be used or generated when a control program and an algorithm program are executed, which will be described further below. Here, the memory 160 may have a ROM (Read Only Memory) or a flash memory to store a control program for achieving a predetermined function in each component such as a sensing operation in the heartbeat sensor 110 and the various sensors 12, a vibrating operation in the vibration section 140, and a data transmitting operation in the communication module 170, and an algorithm program for achieving a biological information notifying method for notifying the user US by generating vibrations of a predetermined vibration pattern corresponding to the heartbeat from the vibration section 140 based on the above-described heartbeat data. The entire or part of the non-volatile memory portion forming the memory 160 may be in a form of a removable storage medium such as a memory card, and may be structured to be removable from the apparatus main body 101.

The control section 150 has a clock function and, by performing processing by following the above-described control program stored in the memory 160, controls the operation in each component, such as the sensing operation in the heartbeat sensor 110 and the various sensors 120, the vibrating operation in the vibration section 140, and the data transmitting operation in the communication module 170, to achieve a predetermined function. Also, by performing processing by following the above-described algorithm program stored in the memory 160, the control section 150 achieves the biological information notifying method for notifying the user US by generating vibrations of a predetermined vibration pattern corresponding to the heartbeat from the vibration section 140 based on heartbeat data obtained by the heartbeat sensor 110 in the control section 150. The control program and the algorithm program executed in the control section 150 may be incorporated in advance inside the control section 150.

The communication module 170 functions as an interface when heartbeat data obtained from the heartbeat sensor 110, sensor data obtained from the various sensors 120, notification information generated by processing these data by following the above-described algorithm program, or the like is transmitted to an external device or the like provided outside the biological information notifying apparatus 100 (or the apparatus main body 101). Here, as a method for transmitting various data, information, etc., to the external device or the like via the communication module 170, various wireless communication methods, wired communication methods via a communication cable, etc. can be applied. Also, as an external device, for example, an electronic device such as a personal computer, a portable telephone, a smartphone, or a tablet terminal can be applied. According to the communication module 170 described above, various data, information, or the like obtained or generated in the biological information notifying apparatus 100 are displayed on a display device included in the external device for viewing and analyzed in detail after the end of measurement of biological information or after the end of an exercise, whereby it is possible to accurately grasp the user's own health condition and exercise condition.

The power supply section 180 supplies driving electric power to each component inside the apparatus main body 101 of the biological information notifying apparatus 100. As the power supply section 180, for example, a primary battery such as a commercially-available coin-shaped battery or button-shaped battery or a secondary battery such as a lithium-ion battery or a nickel metal hydride battery can be applied. Furthermore, as the power supply section 180, in addition to these primary battery and secondary battery, it is possible to apply a power supply by energy harvest technology for generating electricity by energy such as vibrations, light, heat, or electro-magnetic waves.

(Biological Information Notifying Method)

Next, the biological information notifying method in the biological information notifying apparatus according to the present embodiment is described.

Figure 4A:
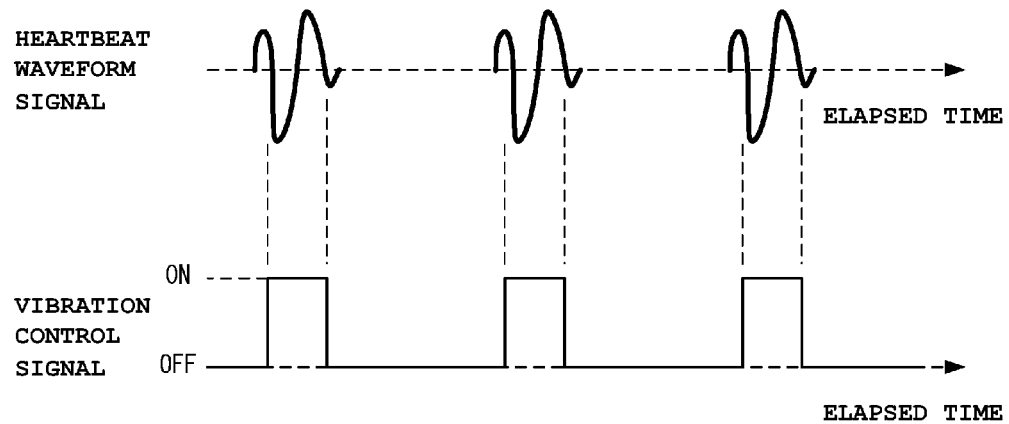
FIG. 4A and FIG. 4B are signal waveform diagrams depicting examples of a pattern of vibrations by the biological information notifying method according to the first embodiment.
Figure 4B:
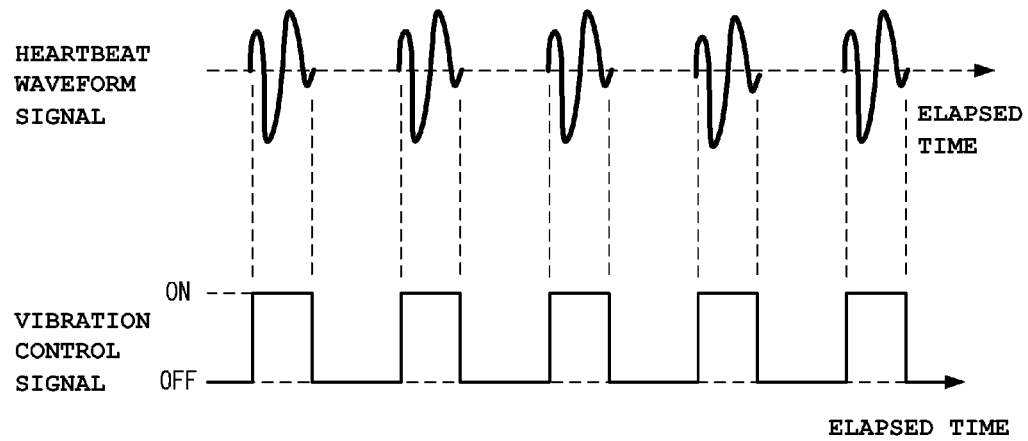

FIG. 3 is a flowchart of an example of the biological information notifying method in the biological information notifying apparatus according to the present embodiment. FIG. 4A and FIG. 4B are signal waveform diagrams showing examples of a pattern of vibrations by the biological information notifying method according to the present embodiment.

In the biological information notifying method in the biological information notifying apparatus having the above-described structure, the biological information notifying apparatus 100 is first started to cause the control section 150 to start the sensing operation in the heartbeat sensor 110 and the various sensors 120, as depicted in FIG. 3. Specifically, the user US operates the operation switch 130 provided to the apparatus main body 101 of the biological information notifying apparatus 100 worn on the chest part, so as to turn on and activate the biological information notifying apparatus 100, and the control section 150 starts a sensing operation in the heartbeat sensor 110 and the various sensors 120. As a result, heartbeat data of the user US is detected by the heartbeat sensor 110, and various sensor data associated with the exercise condition and biological state of the user US are detected by the various sensors 120 (Step S101). These heartbeat data and various sensor data are stored in a predetermined storage area of the memory 160 in association with each other for each detection time in each sensor.

Next, based on the detected heartbeat data, the control section 150 causes vibrations corresponding to the heartbeat timing to be generated, and causes the user US to be notified of heartbeat information from the biological information notifying apparatus 100 (Step S102). Specifically, as depicted in FIG. 4A and FIG. 4B, with the timing of a heartbeat waveform signal (corresponding to a waveform output of the above-described electrocardiographic signal) detected by the heartbeat sensor 110, a vibration control signal is outputted from the control section 150 to the vibration section 140. Then, the vibration section 140 generates vibration with a predetermined vibration strength for a period corresponding to the signal width of the received vibration control signal. Here, the above-described corresponding timing detected by the control section 150 is stored in a predetermined storage area of the memory 160.

That is, in general, the heart rate of a person at the time of resting, walking, or the like is approximately 60 to 80 per minute and, in response to this heart rate, the vibration section 140 generates 60 to 80 vibrations per minute corresponding to all heartbeats (refer to FIG. 4A). Also, the heart rate of the person at the time of running, a hard exercise, or the like is approximately twice or third times as high as that at the time of resting, walking, or the like and, for example, may reach 180 or 200 per minute. In this case as well, the vibration section 140 generates 180 or 200 vibrations per minute correspondingly to all heartbeats (refer to FIG. 4B). As a result, the entire apparatus main body 101 or a portion near the vibration section 140 of the biological information notifying apparatus 100 vibrates to transmit heartbeat information to the body of the user US that is in close contact with the biological information notifying apparatus 100 via these vibrations.

In the present embodiment, the vibrations generated by the vibration section 140 are set to have a predetermined vibration time and vibration strength. These vibration time and vibration strength may be arbitrarily set by, for example, the user US operating the operation switch 130 or the like.

Next, the control section 150 repeats the above-described heartbeat detecting operation (Step S101) and the corresponding vibrating operation (Step S102) until an instruction for ending the processing is provided (Step S103). Here, the instruction for ending the processing is generated by, for example, the user US operating the operation switch 130 to end the sensing operation in the heartbeat sensor 110 and the various sensors 120 or powering off the biological information notifying apparatus 100 for stopping.

As such, in the present embodiment, the heartbeat of the user US is continuously detected by the heartbeat sensor 110 of the biological information notifying apparatus 100 worn on the body of the user US, and vibrations corresponding to the heartbeat are generated by the vibration section 140, whereby the body of the user US that is in close contact with the biological information notifying apparatus 100 is notified of heartbeat information. As a result, the user US can tactually sense the vibrations and intuitively grasp his or her own heart rate or a change thereof in real time based on the sensing timing and cycle.

Also, here, unlike the related art described above, there is no need to perform a motion of raising an arm or temporarily stop a motion during an exercise in order to visually check the heart rate or the like displayed on a display section of a heartbeat measuring apparatus worn on a wrist. Therefore, irrespective of exercise details, exercise position, fatigue condition, etc., the user can easily grasp his or her heart rate and a change thereof in real time without performing a special motion.

Specifically, while the user US is performing an exercise such as running or jogging, the user himself or herself who is a runner can grasp in real time a change in heartbeat when the pitch is increased; a change in heartbeat when the stride is extended; a change in heartbeat in a course environment such as a slope, a gravel road, or a roadway; a change in heartbeat when the user is overtaken by others; a change in heartbeat when a breathing method is changed; a change in heartbeat when the swing of the arms or the position is changed; or the like. Accordingly, a change in heartbeat in various situations can be grasped during an exercise, which contributes to a prompt finding of a better exercise method (for example, an improvement and contrivance in the running method), compared with the case where such a change is displayed and analyzed by using an external device such as a personal computer at home after the exercise.

Second Embodiment

Next, a second embodiment of the biological information notifying method in the biological information notifying apparatus according to the present invention is described. Note that the second embodiment is described with reference to the structure described in the above-described first embodiment (FIG. 1A, FIG. 1B and FIG. 2) as appropriate.

In the biological information notifying method described in the first embodiment, vibrations are generated by the vibration section 140, corresponding to all the heartbeats of the user US detected by the heartbeat sensor 110. In the method of the second embodiment, vibrations corresponding to all the heartbeats of the user US detected by the heartbeat sensor 110 are generated by the vibration section 140 only when the heartbeat of the user US detected by the heartbeat sensor 110 is within a predetermined threshold range.

Figure 6A:
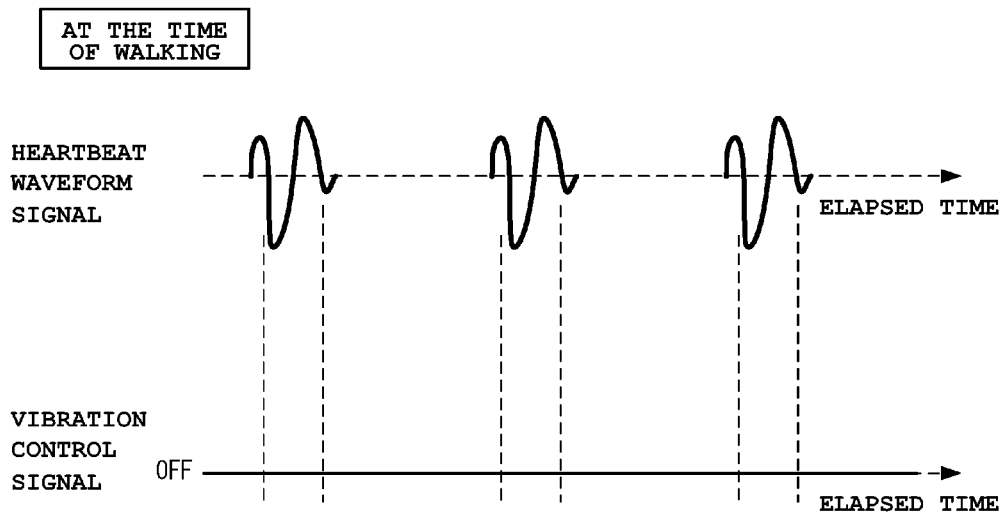
FIG. 6A and FIG. 6B are signal waveform diagrams depicting examples of a pattern of vibrations by the biological information notifying method according to the second embodiment.
Figure 6B:
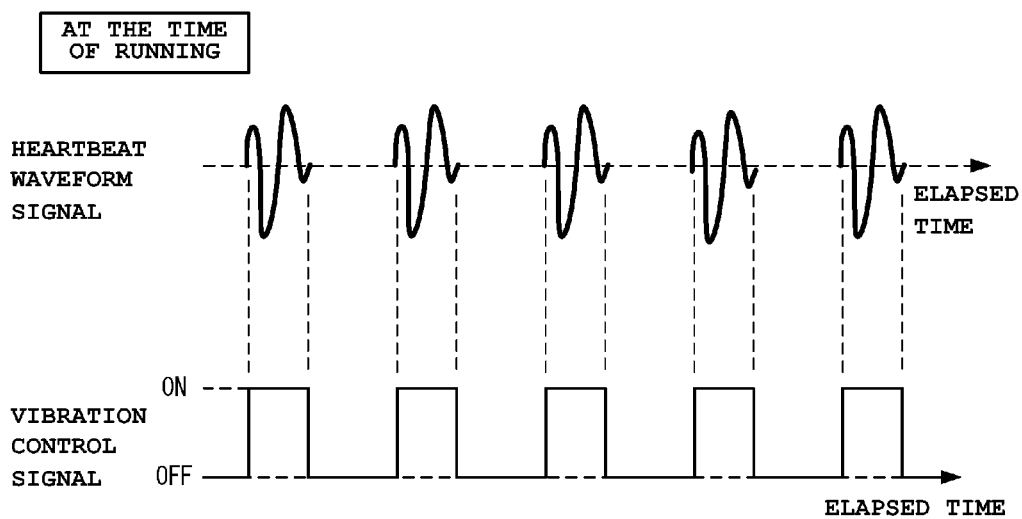

FIG. 5 is a flowchart of an example of the biological information notifying method according to the second embodiment. FIG. 6A and FIG. 6B are signal waveform diagrams showing examples of a pattern of vibrations by the biological information notifying method according to the present embodiment. Here, processing identical to that of the above-described first embodiment is simply described.

In the biological information notifying method according to the second embodiment, in a biological information notifying apparatus having a structure similar to that of the first embodiment described above (refer to FIG. 1A, FIG. 1B and FIG. 2), the control section 150 first sets a threshold range regarding a heart rate (Step S201), as depicted in FIG. 5. Specifically, after the biological information notifying apparatus 100 is turned on to start, the control section 150 sets an arbitrary heart rate that serves as a threshold by the user US operating the operation switch 130. Here, the threshold range may be set by, for example, specifying a specific heart rate such as 120 times per minute and taking a range equal to or more than the heart rate as a threshold range, or by specifying a numerical value range in which the lower-limit value is 120 times per minute and the upper-limit value is 200 times per minute so as to set a threshold range. As a method for setting this threshold range, a scheme may be applied in which the user US operates the operation switch 130 to directly input and set a numerical value of the heart rate. Also, a scheme may be applied in which a plurality of thresholds are prepared in advance such as 120 times per minute, 140 times per minute and 160 times per minute, and the user US operates the operation switch 130 to select one of these thresholds for setting.

Next, as with the heartbeat detecting operation (Step S101) in the above-described first embodiment, the control section 150 starts a sensing operation in the heartbeat sensor 110 and the various sensors 120 to detect heartbeat data and various sensor data of the user US (Step S202). The detected heartbeat data and various sensor data are stored in a predetermined storage area of the memory 160 in association with each other for each detection time.

Next, the control section 150 measures a heart rate per unit time based on the detected heartbeat data, and judges whether the measured heart rate is within the threshold range set in advance (Step S203). Specifically, when the heart rate per minute is set as a threshold in the above-described threshold range setting operation (Step S201), the control section 150 measures the heart rate of the user US based on the latest heartbeat data per minute among the data stored and accumulated in the memory 160. Next, the control section 150 performs processing for comparing the measured heart rate and the threshold range set in advance.

Then, when judged that the measured heart rate is within the threshold range set in advance, as with the corresponding vibration operation in the first embodiment described above (Step S102), the control section 150 generates vibrations at the heartbeat timing and notifies the user US as heartbeat information (Step S204). Specifically, in a case where a threshold of, for example, 120 times per minute has been set in the above-described threshold range setting operation (Step S201), when the measured heart rate exceeds 120 times per minute, the control section 150 controls the vibration section 140 to generate vibrations corresponding to all heartbeats based on the measured heart rate. On the other hand, when judged that the measured heart rate is out of the threshold range set in advance, the control section 150 continues the heartbeat detecting operation (Step S202) without causing the vibration section 140 to vibrate.

That is, when the heart rate measured by the control section 150 is out of the threshold range set in advance, such as when the user US is resting or walking, a vibration control signal is not outputted from the control section 150 to the vibration section 140 even if a heartbeat waveform signal is detected, as depicted in FIG. 6A. Therefore, the vibration section 140 is not vibrated. On the other hand, when the heart rate measured by the control section 150 is within the threshold range set in advance, such as when the user US is running or performing a hard exercise (or when the heart rate is equal to or larger than the threshold set in advance), a vibration control signal is outputted from the control section 150 to the vibration section 140 at the timing of the heartbeat waveform signal, as depicted in FIG. 6B, whereby the vibration section 140 is vibrated. As a result, heartbeat information is transmitted by the vibrations to the body of the user US that is in close contact with the biological information notifying apparatus 100.

Next, the control section 150 repeats a series of processing for the threshold range setting operation (Step S201), the heartbeat detecting operation (Step S202), the threshold range judging operation (Step S203), and the corresponding vibration operation (Step S204) until an instruction for ending the processing is provided (Step S205).

As such, in the present embodiment, vibrations corresponding to the heartbeat are generated by the vibration section 140 and the user US is notified of heartbeat information only when the heart rate of the user US is within the threshold range set in advance. This can support the case where the heart rate and a change thereof are desired to be accurately grasped in real time only when the heart rate is within a specific range, the case where there is no need to always sense vibrations corresponding to the heartbeat, or the case where it is bothersome or annoying to always sense vibrations corresponding to the heartbeat. Also, a change from a low heart rate state to a high heart rate state within a specific range can be intuitively grasped by vibrations.

In the present embodiment as well, since the user US is notified of heartbeat information by vibrations corresponding to the heartbeat, he or she can easily and intuitively grasp the heart rate and a change thereof in real time without performing a motion of raising an arm, temporarily stopping a motion during an exercise, or performing a special motion, as with the above-described first embodiment.

Third Embodiment

Next, a third embodiment of the biological information notifying method in the biological information notifying apparatus according to the present invention is described. Note that the third embodiment is also described with reference to the structure described in the above-described first embodiment (FIG. 1A, FIG. 1B and FIG. 2) as appropriate.

In method of the above-described first or second embodiment, vibrations are generated with the same vibration strength corresponding to all heartbeats detected by the heartbeat sensor 110 or all heartbeats within a specific threshold range. In the method of the third embodiment, a strong or weak pattern of vibrations is set in advance, and vibrations are generated corresponding to all heartbeats, with the set vibration strength (strong/weak pattern).

Figure 7:
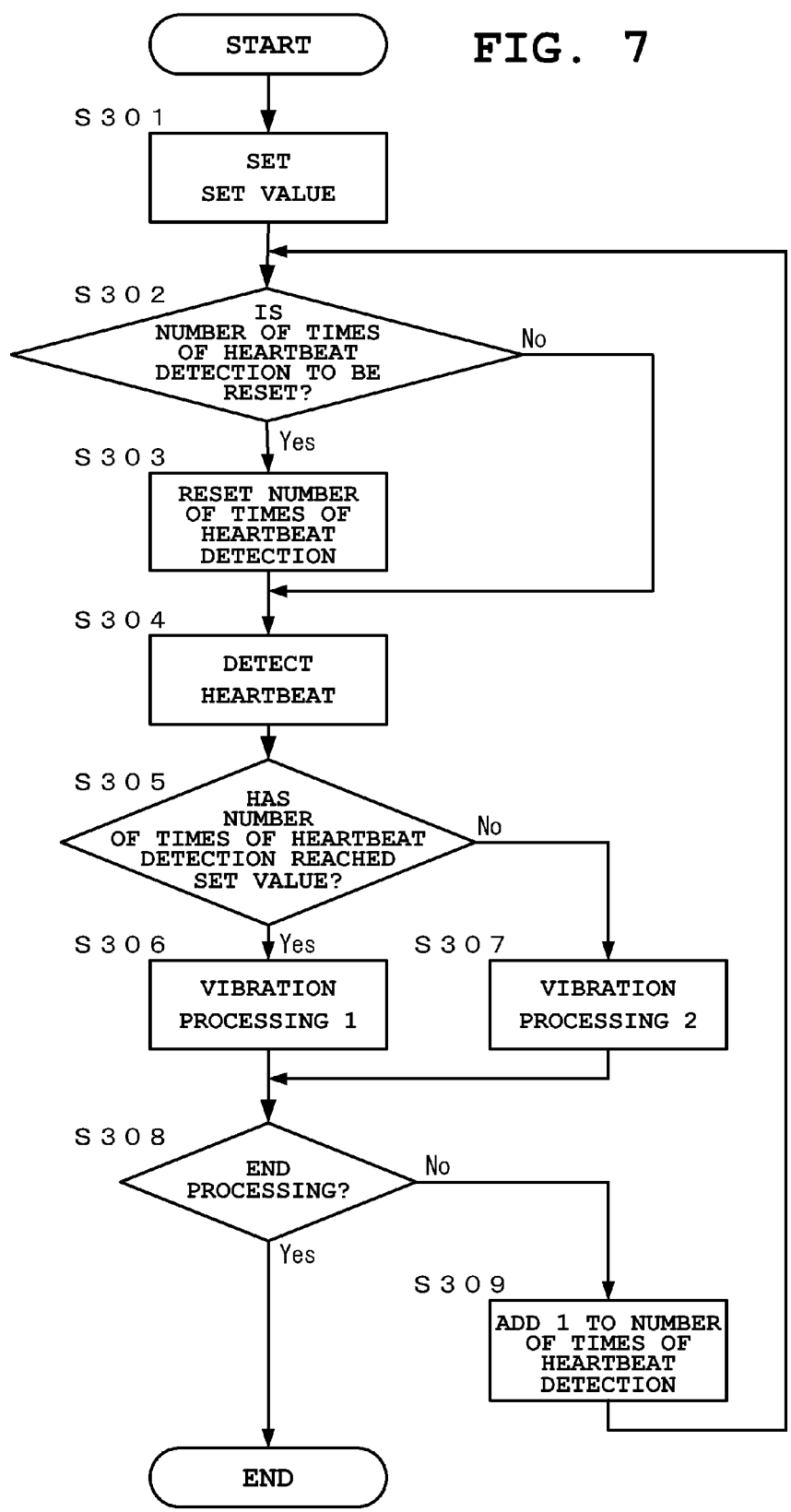
FIG. 7 is a flowchart of an example of a biological information notifying method according to a third embodiment.
Figure 8:
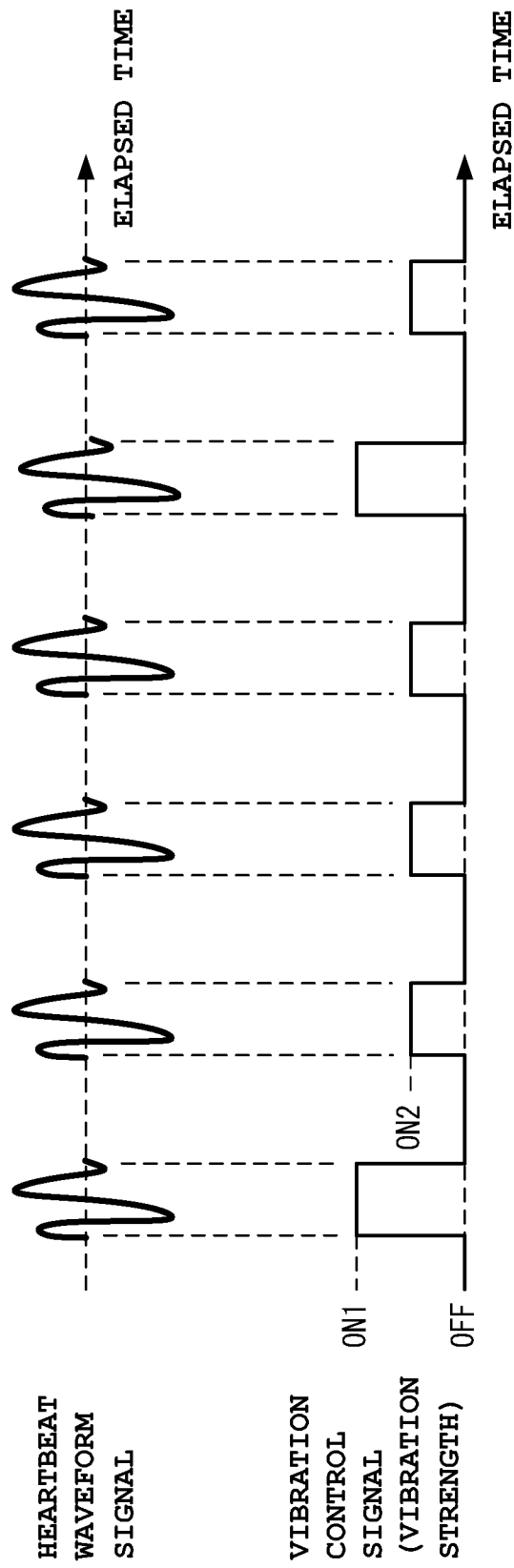
FIG. 8 is a signal waveform diagram depicting example of a pattern of vibrations by the biological information notifying method according to the third embodiment.

FIG. 7 is a flowchart of an example of the biological information notifying method according to the third embodiment. FIG. 8 is a signal waveform diagram showing an example of a pattern of vibrations performed by the biological information notifying method according to the present embodiment. Here, processing identical to that of the above-described first or second embodiment is simply described.

In the biological information notifying method according to the third embodiment, in a biological information notifying apparatus having a structure similar to that of the above-described first embodiment (refer to FIG. 1A, FIG. 1B and FIG. 2), the control section 150 first sets a set value regarding a strong/weak pattern of vibrations corresponding to heartbeat (Step S301), as depicted in FIG. 7. Specifically, after the biological information notifying apparatus 100 is turned on to start, the user US operates the operation switch 130 to set a set value defining a strong/weak pattern of vibrations. Here, the strong/weak pattern of vibrations (a vibration pattern) indicates how the strength of vibrations generated by the vibration section 140 changes with respect to continuous heartbeats. For example, a set value is set that defines a vibration pattern such that a strong vibration is generated once in several times and weak vibrations are generated in other cases or such that a vibration is generated only once in several times. As a method for setting a vibration pattern, a scheme may be applied where the user US operates the operation switch 130 to directly input and set a set value. Also, a scheme may be applied where a plurality of thresholds are prepared in advance, and the user US operates the operation switch 130 to select an arbitrary vibration pattern for setting.

Next, the control section 150 judges whether it is required to reset the number of times of heartbeat detection for use in judging processing (which will be described in detail further below) that is performed to achieve the above-described vibration pattern (Step S302). When judged that it is required to reset the number of times of heartbeat detection, the control section 150 sets (resets) a count value of the number of times of heartbeat detection to "0" or "1" (Step S303), and performs a heartbeat detecting operation as with the above-described first embodiment (Step S304). Here, the case where it is required to reset the number of times of heartbeat detection refers to the case in the biological information notifying method according to the present embodiment where the number of times of heartbeat detection has reached a set value set in advance, the case where the biological information notifying apparatus 100 has been activated to start a sensing operation in the heartbeat sensor 110, or the case where the user US has operated the operation switch 130 to forcibly reset the number of times of detection.

On the other hand, when judged at the above-described reset judging operation (Step S302) that it is not required to reset the number of times of heartbeat detection, the control section 150 performs a heartbeat detecting operation without resetting the count value of the number of times of heartbeat detection (Step S304). Note that the case where it is not required to reset the number of times of heartbeat detection indicates the case where the number of times of heartbeat detection has not reached the set value set in advance in the biological information notifying method according to the present embodiment.

Next, the control section 150 judges whether the number of times of heartbeat detection in the above-described heartbeat detecting operation (Step S304) has reached the set value set in advance (Step S305). Specifically, when, for example, a set value defining a vibration pattern is set in the above-described set value setting operation (Step S301) where a strong vibration is generated once in four times and a weak vibration is generated at the remaining three times for continuous heartbeats (in this case, "4" is set, for example), the control section 150 judges whether the number of times of heartbeat detection at this point has reached the set value. Then, when judged that the number of times of heartbeat detection has reached the set value, the control section 150 outputs a vibration control signal for performing vibration processing 1 for causing the vibration section 140 to strongly vibrate (corresponding to "ON1" in the drawing) as depicted in FIG. 8, and thereby causes the vibration section 140 to vibrate with a high vibration strength.

On the other hand, when judged that the number of times of heartbeat detection has not reached the set value, the control section 150 outputs a vibration control signal for performing vibration processing 2 for causing the vibration section 140 to weakly vibrate (corresponding to "ON2" in the drawing) as depicted in FIG. 8, and thereby causes the vibration section 140 to vibrate with a low vibration strength. As a result, heartbeat information is transmitted to the body of the user US that is in close contact with the biological information notifying apparatus 100 by vibrations with the vibration pattern where a strong vibration is generated once in four times and a weak vibration is generated at the remaining three times in response to the detected heartbeat, as depicted in FIG. 8.

Next, the control section 150 judges whether an instruction for ending the series of processing described above has been provided (Step S308). When an instruction for ending the processing has not been provided, the control section 150 adds "1" to the count value of the number of times of heartbeat detection (Step S309), and returns to the above-described reset judging operation (Step S302) to repeatedly perform the series of processing.

As such, in the present embodiment, the user US is notified of heartbeat information by, for example, a strong vibration being generated only once in a predetermined number of times in response to a heartbeat and weak vibrations being generated for the remaining heartbeats, among the detected heartbeat data of the user US. As a result, even when the heart rate is increased to, for example, 160 times per minute or 180 times per minute, the user US can accurately grasp the heart rate and a change thereof in real time. Also, the present embodiment can support the cases where there is no need to continuously sense a constant vibration corresponding to the heartbeat and where it is bothersome or annoying to continuously sense a constant vibration corresponding to the heartbeat.

Note that the biological information notifying method according to the present embodiment is not limited to the case of performing a series of processing alone and, for example, may be performed in combination with the scheme of the biological information notifying method described in the second embodiment. That is, a configuration may be adopted in which a predetermined threshold range is set in advance and, when the heart rate is not within the predetermined threshold range, vibrations having the same vibration strength are generated for all heartbeats, or no vibration is generated. In this configuration, only when the heart rate is within the predetermined threshold range, a strong vibration is generated once in predetermined number of times in response to a heartbeat, and weak vibrations are generated for the remaining times. As a result, the user US can sense that the heart rate has entered the predetermined threshold range, and can simply and intuitively grasp the heart rate or a change thereof within the threshold range.

Fourth Embodiment

Next, a fourth embodiment of the biological information notifying method in the biological information notifying apparatus according to the present invention is described. Note that the fourth embodiment is also described with reference to the structure described in the above-described first embodiment (FIG. 1A, FIG. 1B and FIG. 2) as appropriate.

In the method of the above-described second or third embodiment, vibrations having the same vibration strength are generated corresponding to all heartbeats within the specific threshold range, among heartbeat data detected by the heartbeat sensor 110, or a vibration having a different vibration strength is generated for a heartbeat for each specific time. In the method of the fourth embodiment, the strength and length (period) of vibrations are switched and set according to the increase or decrease of the heart rate and the presence or absence of a change thereof, and then the vibrations are generated.

Figure 9:
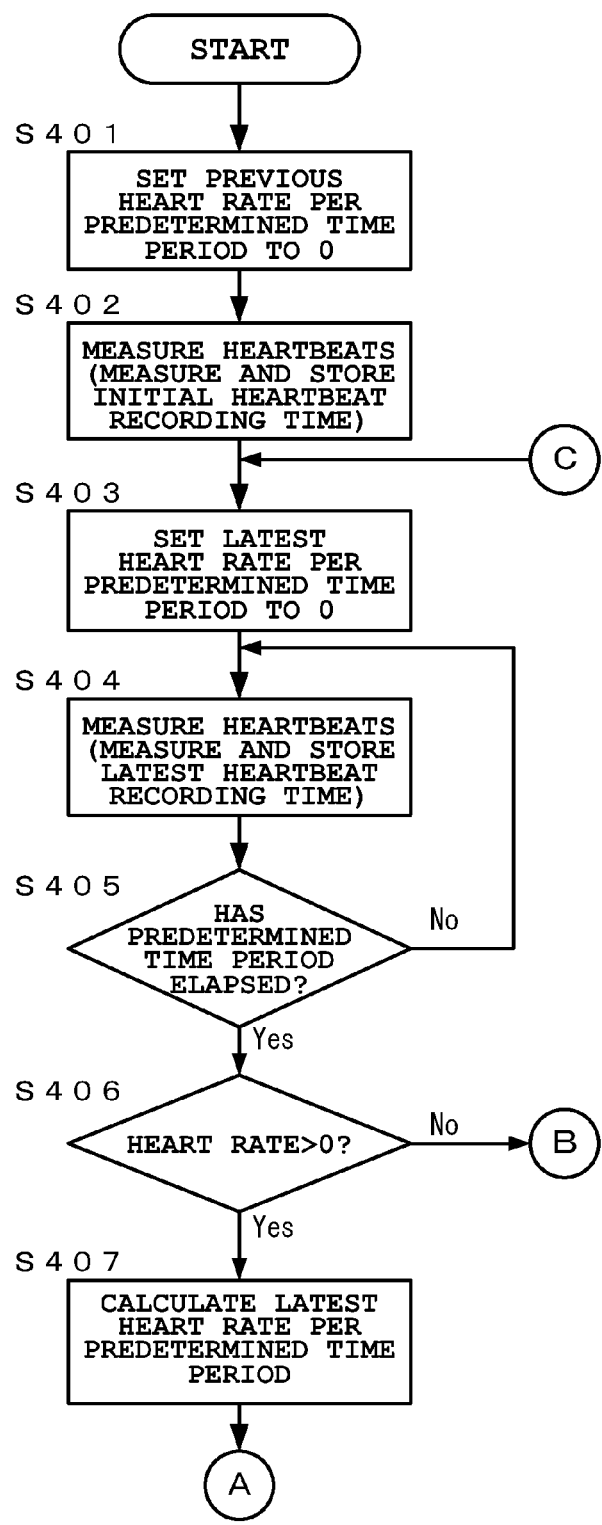
FIG. 9 is a first flowchart of an example of a biological information notifying method according to a fourth embodiment.
Figure 10:
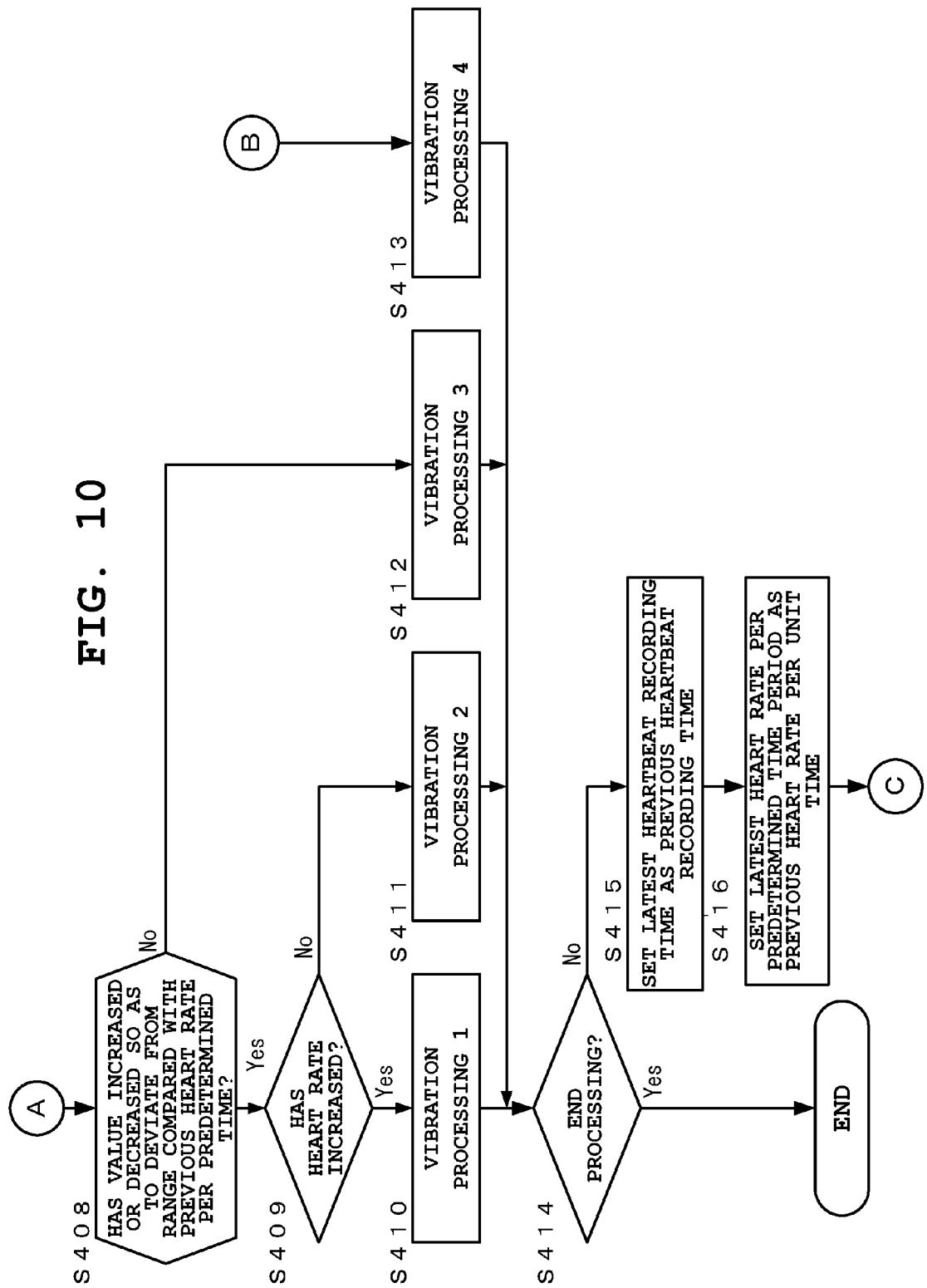
FIG. 10 is a second flowchart of the example of the biological information notifying method according to the fourth embodiment.

FIG. 9 and FIG. 10 are flowcharts of an example of the biological information notifying method according to the fourth embodiment. Here, processing identical to those of the above-described first to third embodiments is simply described.

In the biological information notifying method according to the fourth embodiment, in a biological information notifying apparatus having a structure similar to that of the above-described first embodiment (refer to FIG. 1A, FIG. 1B, and FIG. 2), the control section 150 first sets (resets) a previous count value of the heart rate per a predetermined time period to "0" (Step S401) as depicted in FIG. 9, and then starts the heartbeat detecting operation, as with the first embodiment described above. Here, the control section 150 causes the initially-detected detection time of the heartbeat to be measured as a heartbeat recording time and stored in the memory 160 (Step S402).

Next, after setting (resetting) the current (or the latest) heart rate per a predetermined time period to "0" (Step S402), the control section 150 measures the latest heartbeat detection time (heartbeat recording time) detected by the heartbeat detecting operation, stores the measured detection time in the memory 160 (Step S404), and performs processing for adding "1" to the count value of the heart rate.

Next, in the latest heart rate resetting operation (Step S403), the control section 150 judges whether the time elapsed from when the heart rate per the predetermined time period has been set to "0" has reached the predetermined time (Step S405). When judged that the elapsed time has not reached the predetermined time, the control section 150 repeatedly performs the operation of measuring the latest heartbeat detection time (heartbeat recording time) (Step S404). On the other hand, when judged that the elapsed time has reached the predetermined time, the control section 150 judges whether the heart rate per the predetermined time period is 0 or another value (heart rate>0) (Step S406). That is, for example, when the predetermined time period has been set to a relatively short time such as 0.5 seconds, if the current state is a state where the heart rate is low such as when the user US is resting, a heartbeat may not be detected within the predetermined time period. Accordingly, whether or not a heartbeat has been detected within the predetermined time period is judged and, if a heartbeat has not been detected (that is, if the heart rate is "0"), the control section 150 performs processing for, for example, preventing the vibration section 140 from vibrating (vibration processing 4), as depicted in FIG. 10 (Step S413).

On the other hand, when a heartbeat has been detected within the predetermined time period (that is, heart rate>0), the control section 150 extracts the latest heartbeat recording time and the previous heartbeat recording time stored in the memory 160 and, based on the difference therebetween and the heart rate therebetween, calculates the latest heart rate per the predetermined time period (Step S407). Specifically, computation processing represented by the following equation is performed. Note that the previous heartbeat recording time herein is the latest heartbeat recording time used when the previous heart rate per the predetermined time period is calculated.

(the latest heart rate per the predetermined time period)=(the heart rate)/(the latest heartbeat recording time–the previous heartbeat recording time)

Next, the control section 150 compares the previous heart rate per the predetermined time period with the calculated latest heart rate per the predetermined time period to judge whether the difference therebetween (that is a change in the heart rate) is within a predetermined judgment range (Step S408), as depicted in FIG. 10. Note that the predetermined judgment range herein is a range set in advance as a range where it is difficult to judge a change of an increase or decrease due to fluctuations of the heart rate per the predetermined time period. Then, when judged that the difference (the change in the heart rate) is within the predetermined judgment range, the control section 150 performs vibration processing 3 for, for example, vibrating the vibration section 140 with a third vibration for a short period (Step S412).

On the other hand, when judged that the difference (the change in the heart rate) is out of the predetermined judgment range, the control section 150 judges whether the change in the heart rate corresponding to the difference is an increase or decrease (whether the heart rate has been increased) (Step S409). When judged that the heart rate has been increased, the control section 150 performs vibration processing 1 for, for example, vibrating the vibration section 140 strongly with a first vibration (Step S410). When judged that the heart rate has been decreased, the control section 150 performs vibration processing 2 for, for example, vibrating the vibration section 140 weakly with a second vibration (Step S411). That is, the first vibration has an amplitude larger than that of the second vibration, and the third vibration has a vibration period shorter than those of the first vibration and the second vibration.

Also, here, the vibration period of the first vibration may be equal to the vibration period of the second vibration, and the amplitude of the third vibration may be smaller than the amplitude of the first vibration and may be larger than the amplitude of the second vibration.

As a result, heartbeat information is transmitted to the body of the user US that is in close contact with the biological information notifying apparatus 100 by vibrations of various vibration patterns corresponding to the heartbeat in a manner that a strong vibration is generated when the heart rate is significantly increased, a weak vibration is generated when the heart rate is significantly decreased, a vibration is generated for a short time when the heart rate is slightly changed within the predetermined judgment range, and no vibration is generated when no heartbeat is detected.

Next, the control section 150 judges whether an instruction for ending the above-described series of processing has been provided (Step S414). When an instruction for ending the processing has not been provided, the control section 150 sets the latest heartbeat storage time as the previous heartbeat storage time, stores the set time in the memory 160 (Step S415), sets the latest heart rate per the predetermined time period as the previous heart rate per the predetermined time period, and stores the set heart rate in the memory 160 (Step S416). Then, the control section 150 returns to the latest heart rate reset operation (Step S403) to repeatedly perform the series of processing.

As such, in the present embodiment, heart rates per a predetermined time period are sequentially calculated based on the detected heartbeat data of the user US. Then, according to an increase or decrease of the heart rate or the presence or absence of a change in the heart rate judged by comparing the latest heart rate and the immediately preceding heart rate, vibrations are generated with a vibration strength and length set corresponding to the heartbeat, whereby the user US is notified of heartbeat information. As a result, the user US can accurately grasp the heart rate or a change thereof in real time by sensing a change in the vibration pattern. Also, the present embodiment can support the cases where there is no need to continuously sense a constant vibration corresponding to the heartbeat and where it is bothersome or annoying to continuously sense a constant vibration corresponding to the heartbeat.

<Other Examples of Structure of Biological Information Notifying Apparatus>

Next, other examples of the structure of the biological information notifying apparatus according to the present invention are described.

In each embodiment described above, the biological information notifying apparatus is described which has an outer appearance of a chest sensor that is worn on the chest part of the user US and includes the heartbeat sensor 110, the various sensors 120, the vibration section 140, the control section 150, the memory 160, etc. incorporated therein. However, the present invention is not limited thereto. For example, as will be described in a first structural example further below, the biological information notifying apparatus may have an outer appearance of a wristwatch or a wristband that is worn on a wrist or the like of the user US. Alternatively, as will be described in a second structural example further below, the biological information notifying apparatus may have a sensor device of a chest sensor type and an interface device of a wristwatch type.

(First Structural Example)

FIG. 11A and FIG. 11B are schematic structural diagrams depicting another example of the structure (first structural example) of the biological information notifying apparatus according to the preset invention. FIG. 12 is a functional block diagram of the biological information notifying apparatus according to this structural example. Here, components identical to those of the above described first embodiment are provided with the same reference numerals for simplification of description.

The biological information notifying apparatus according to the first structural example is worn on a wrist of the user US, as depicted in FIG. 11A. For example, as depicted in FIG. 11B, a biological information notifying apparatus 200 has an outer appearance of a wristwatch or a wristband, and mainly includes an apparatus main body 201 having a function of detecting various biological information including the heart rate of the user US and a belt section 202 that is wound around a wrist of the user US to mount the apparatus main body 201 on the wrist.

Specifically, the apparatus main body 201 mainly includes a heartbeat sensor 210, various sensors 220, an operation switch 230, a vibration section 240, a control section 250, a memory 260, a communication module 270, a power supply section 280, and a display section 290, as depicted in FIG. 12. Note that the structures except that of the display section 290, that is, the structures of the heartbeat sensor 210, the various sensors 220, the operation switch 230, the vibration section 240, the control section 250, the memory 260, the communication module 270, and the power supply section 280 are substantially similar to those of the heartbeat sensor 110, the various sensors 120, the operation switch 130, the vibration section 140, the control section 150, the memory 160, the communication module 170, and the power supply section 180, respectively, described in the above-described first embodiment.

The display section 290 has a display panel of a liquid-crystal type or an organic EL type, and displays at least various biological information and exercise information of the user when resting and exercising, by using a numerical value, a character, an image, etc. On the display section 290, numerical value information and character information such as a current time, a heart rate, an exercise time (for example, a running time) are displayed, as depicted in FIG. 11B.

Note that the operation switch 230 in the present structural example may be a button switch provided to the apparatus main body 201 as depicted in FIG. 11B, or may be included in a touch panel provided on the front surface of the display section 290 described above. Also, a structure including both switches may be adopted.

In the above-structured biological information notifying apparatus 200 as well, by applying one of the biological information notifying methods in the above-described embodiments, vibrations having a predetermined vibration pattern can be generated by the vibration section 240 in response to the heartbeat detected by the heartbeat sensor 210, and be transmitted to the body of the user US for notification of heartbeat information. Accordingly, by tactually sensing vibrations, the user US can intuitively grasps his or her heart rate and a change thereof in real time.

In particular, in the present structural example, the display section 290 is provided to the biological information notifying apparatus 200. Therefore, by viewing numerical value information and the like displayed on the display section 290 with respect to heartbeat information transmitted by vibrations, the heart rate and a change thereof can be grasped not only tactually but also visually. Note that a configuration may be adopted in which, in accordance with a judgment result in the threshold range judging operation (Step S203), the heart rate change judging operation (Step S408), the heart rate increase/decrease judging operation (Step S409), or the like in the above-described biological information notifying method, a visual effect is also provided, such as highlighting or flashing the above-described numerical value information and illuminating a background portion of the display section with a specific color. As a result, for example, even when the user US cannot clearly sense vibrations transmitted from the biological information notifying apparatus 200 during an exercise, he or she can be reliably notified of heartbeat information by using the display section 290 as supplemental means.

(Second Structural Example)

Figure 13A:
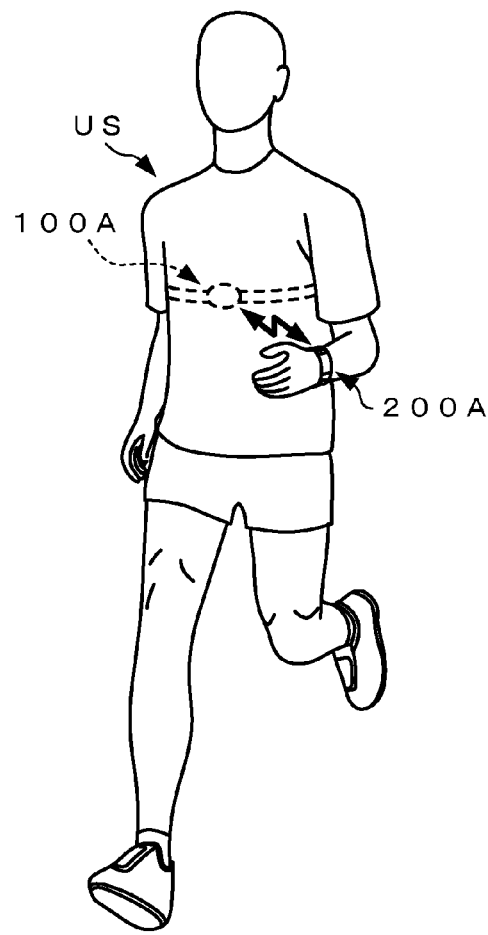
FIG. 13A, FIG. 13B and FIG. 13C are schematic structural diagrams depicting a still another example of the structure of the biological information notifying apparatus according to the present invention (second structural example)
Figure 13C:
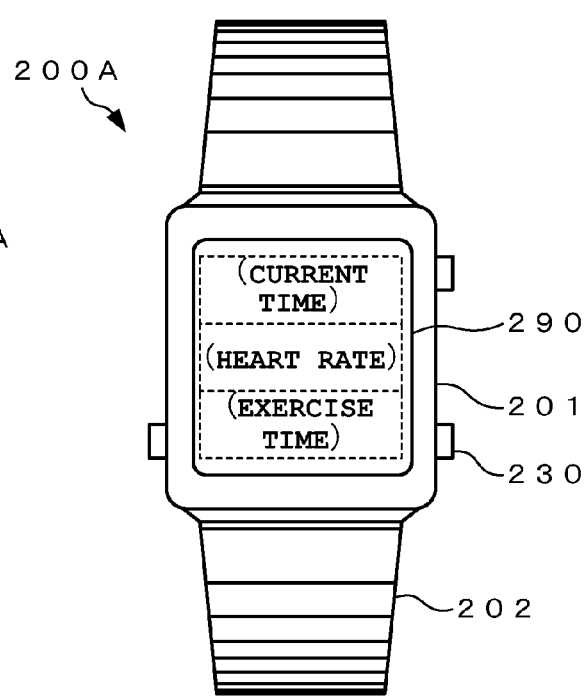
Figure 13B:
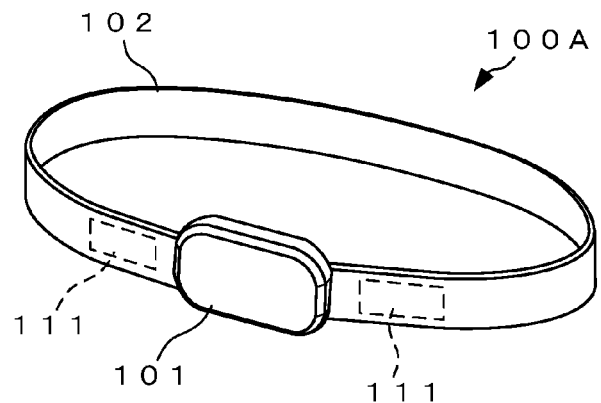
Figure 14A:
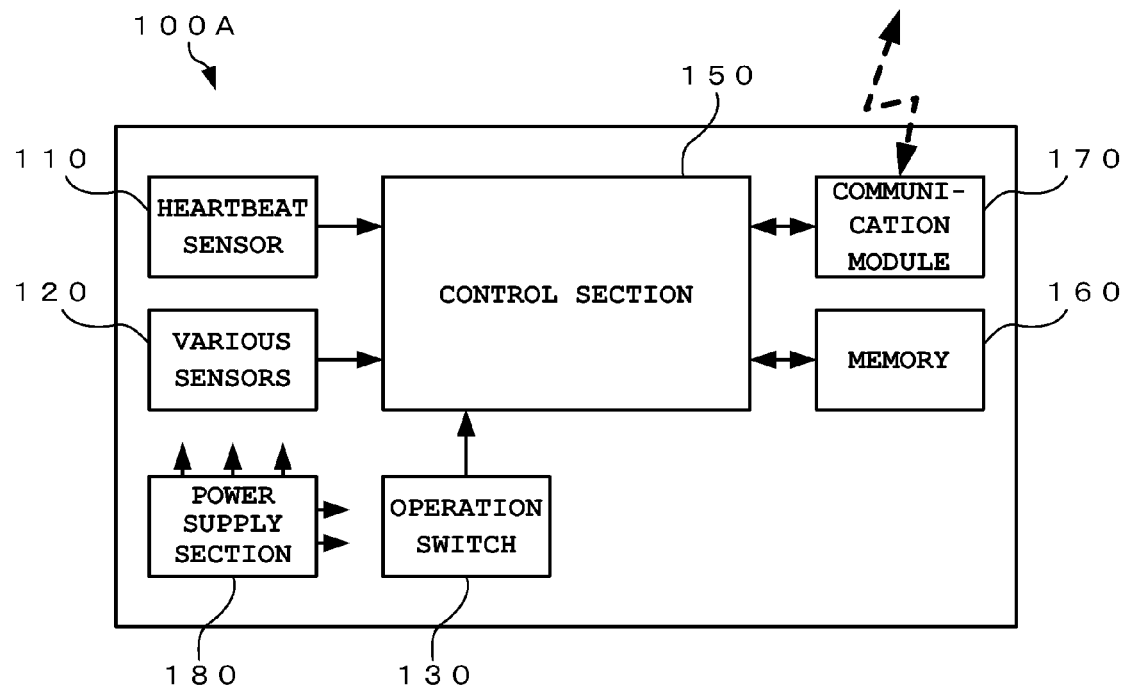
FIG. 14A and FIG. 14B are functional block diagrams of the biological information notifying apparatus according to the second structural example.
Figure 14B:
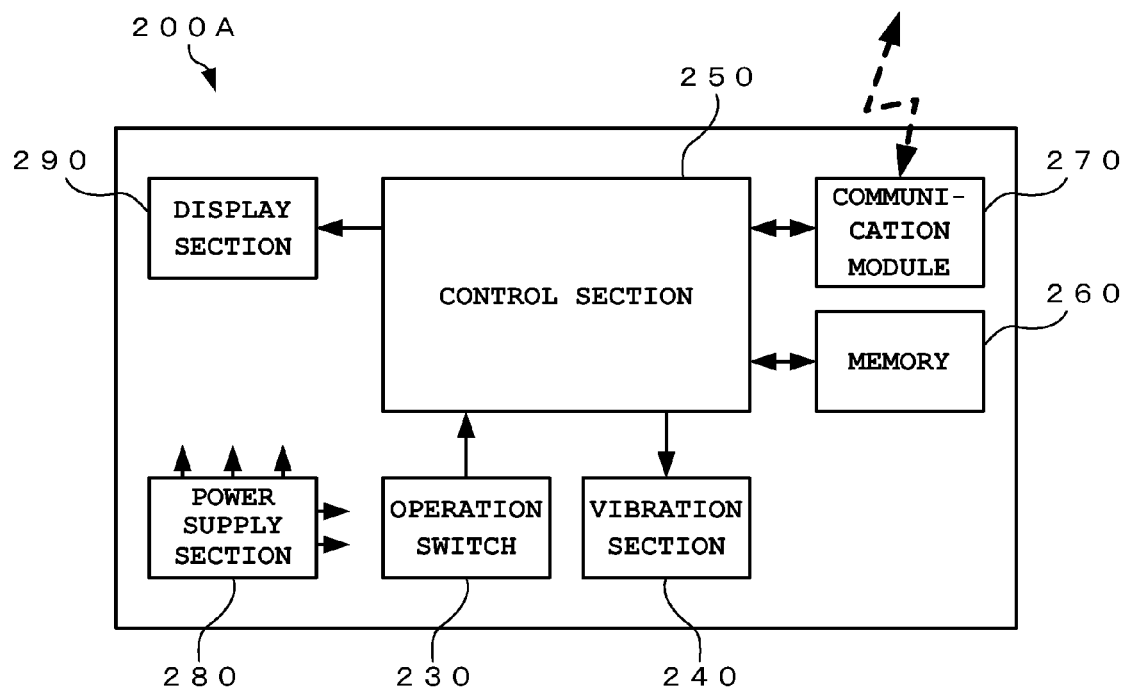

FIG. 13A, FIG. 13B and FIG. 13C are schematic structural diagrams depicting a still another structural example (second structural example) of the biological information notifying apparatus according to the present invention. And FIG. 14A and FIG. 14B are functional block diagrams of the biological information notifying apparatus according to the present structural example. Here, components identical to those of the above-described first embodiment and first structural example are provided with the same reference numerals for simplification of description.

The biological information notifying apparatus according to the second structural example has a sensor device 100A that is worn on the chest part and an interface device 200A that is worn on a wrist of the user US, as depicted in FIG. 13A. Here, as with the above-described first embodiment, the sensor device 100A has an outer appearance of a chest sensor, as depicted in FIG. 13B. Also, as with the above-described first structural example, the interface device 200A has an outer appearance of a wristwatch, as depicted in FIG. 13C.

The sensor device 100A includes the heartbeat sensor 110, the various sensors 120, the operation switch 130, the vibration section 140, the control section 150, the memory 160, the communication module 170, and the power supply section 180, each of which has a structure substantially similar to that of the above-described first embodiment, as depicted in FIG. 14A.

The interface device 200A includes the operation switch 230, the vibration section 240, the control section 250, the memory 260, the communication module 270, the power supply section 280, and the display section 290, each of which has a structure substantially similar to that of the first structural example described above, as depicted in FIG. 14B. The interface device 200A may include some or all of the various sensors 120 except the heartbeat sensor 110 provided to the sensor device 100A.

Here, the communication module 170 of the sensor device 100A and the communication module 270 of the interface device 200A transmit various data between the sensor device 100A and the interface device 200A by, for example, wireless communications. As a wireless communication method regarding a data transmission method between the sensor device 100A and the interface device 200A, Bluetooth (registered trademark), which is a short-range wireless communication standard for digital devices, Bluetooth (registered trademark) low energy planned as a low-power-consumption type in the above-described communication standard, or the like can be favorably applied. Also, as another transmission method applicable to the present embodiment, for example, a wired communication method by a communication cable can also be applied.

In the above-structured biological information notifying apparatus 200 as well, by applying one of the biological information notifying methods of the above-described embodiments, vibrations having a predetermined vibration pattern can be generated by the vibration section 240 provided to the interface device 200A worn on a wrist in response to the heartbeat detected by the heartbeat sensor 110 provided to the sensor device 100A mounted on the chest part, and be transmitted to the body of the user US for notification of heartbeat information.

Here, in the biological information notifying method of each of the above-described embodiments, which processing operation of the series of the processing is to be performed by the sensor device 100A or the interface device 200A can be arbitrarily set. That is, a configuration may be adopted in which the control section 150 in the sensor device 100A performs operations from the sensing operation to the heartbeat detecting operation and further to the vibration pattern judging (deciding) operation, and transmits the detection result and the judgment result to the interface device 200A, and the control section 250 in the interface device 200A generates a vibration control signal to cause the vibration section 240 to vibrate with a predetermined pattern. Also, another configuration may be adopted in which the control section 150 in the sensor device 100A performs operations from the sensing operation to the heartbeat detecting operation and transmits the detection result to the interface device 200A, and the control section 250 in the interface device 200A performs the vibration pattern judging (deciding) operation, generates a vibration control signal based on the judgment result, and cause the vibration section 240 to vibrate with a predetermined vibration pattern.

In particular, in the present structural example, the biological information notifying apparatus is structured as separate devices, that is, the sensor device 100 having the heartbeat sensor 110 and the interface device 200A having the vibration section 240 and the display section 290. As a result, the sensor device 100A can be worn on any part where the heartbeat of the user US can be appropriately detected (sensed). Also, the interface device 200A can be worn on any part where the user US can easily sense vibrations and easily make visual recognition even during an exercise. Therefore, the accuracy of heartbeat data detected by the heartbeat sensor 110 can be enhanced. Also, the user US can be reliably notified of more accurate heartbeat information.

Moreover, the series of processing of the biological information notifying method can be divided between the sensor device 100A and the interface device 200A and performed. Therefore, the processing load on the sensor device 100A and the interface device 200A can be reduced. Also, power consumption in the power supply sections 180 and 280 can be suppressed.

In the above-described embodiments and structural examples, the component of a chest sensor type worn on the chest part of the user US or the component of a wristwatch type or wristband type worn on a wrist of the user US is described as the biological information notifying apparatus. However, the present invention is not limited thereto. That is, the biological information notifying apparatus is only required to be a single electronic device or separate electronic devices including at least a heartbeat sensor and a vibration section. For example, the present invention can be applied to the existing portable telephone, smartphone, eyeglasses-type terminal. Also, the mounting position may be any position as long as the heartbeat of the user can be detected. For example, as long as at least the heartbeat sensor can be worn in an arbitrary form on an arbitrary part of the human body, such as a chest part, a wrist, a fingertip, a palm, or an earlobe, the structure may be any structure.

While the present invention has been described with reference to the preferred embodiments, it is intended that the invention be not limited by any of the details of the description therein but includes all the embodiments which fall within the scope of the appended claims.

What is claimed is:

1. A biological information notifying apparatus comprising:
   a biological information obtainment sensor which detects biological information of a human body;
   a vibration section which notifies the biological information by transmitting vibrations to the human body; and
   a control section which causes the vibration section to vibrate in accordance with the biological information,
   wherein the control section obtains a first count number of the biological information per a predetermined time period at a first time point, and obtains a second count number at a second time point which follows the first time point, and
   wherein the control section causes the vibration section to vibrate with a first vibration in accordance with the biological information, when a difference obtained by subtracting the first count number from the second count number is larger than a positive first value at the second time point.

2. The biological information notifying apparatus according to claim 1, wherein the control section causes the vibration section to vibrate with a second vibration different from the first vibration in accordance with the biological information, when the difference of the biological information is smaller than a negative second value.

3. The biological information notifying apparatus according to claim 2, wherein the control section causes the vibration section to vibrate with a third vibration different from the first vibration and the second vibration in accordance with the biological information, when the difference of the biological information is in a range equal to or smaller than the positive first value and equal to or larger than the negative second value.

4. The biological information notifying apparatus according to claim 3, wherein the first vibration has an amplitude larger than an amplitude of the second vibration, and
   wherein the third vibration has a vibration period shorter than a vibration period of the first vibration and a vibration period of the second vibration.

5. The biological information notifying apparatus according to claim 4, wherein the vibration period of the first vibration is equal to the vibration period of the second vibration, and
   wherein the third vibration has an amplitude smaller than the amplitude of the first vibration and larger than the amplitude of the second vibration.

6. The biological information notifying apparatus according to claim 1, wherein the control section does not cause the vibration section to vibrate, when the second count number of the biological information per the predetermined time period is 0.

7. The biological information notifying apparatus according to claim 1, wherein the biological information obtainment sensor and the vibration section are integrally structured.

8. The biological information notifying apparatus according to claim 1, wherein the biological information obtainment sensor and the vibration section are separately structured.

9. A biological information notifying method comprising:
   a step of detecting biological information of a human body by a biological information obtainment sensor;
   a step of obtaining a first count number of the biological information per a predetermined time period at a first time point, and obtaining a second count number at a second time point which follows the first time point;

a step of causing a vibration section to vibrate with a first vibration in accordance with the biological information, when a difference obtained by subtracting the first count number from the second count number is larger than a positive first value at the second time point; and a step of notifying the biological information by transmitting the vibration to the human body.

10. The biological information notifying method according to claim 9, wherein the vibration section is caused to vibrate with a second vibration different from the first vibration in accordance with the biological information, when the difference of the biological information is smaller than a negative second value.

11. The biological information notifying method according to claim 10, wherein the vibration section is caused to vibrate with a third vibration different from the first vibration and the second vibration in accordance with the biological information, when the difference of the biological information is in a range equal to or smaller than the positive first value and equal to or larger than the negative second value.

12. The biological information notifying method according to claim 11, wherein the first vibration has an amplitude larger than an amplitude of the second vibration, and wherein the third vibration has a vibration period shorter than a vibration period of the first vibration and a vibration period of the second vibration.

13. The biological information notifying method according to claim 12, wherein the vibration period of the first vibration is equal to the vibration period of the second vibration, and wherein the third vibration has an amplitude smaller than the amplitude of the first vibration and larger than the amplitude of the second vibration.

14. The biological information notifying method according to claim 9, wherein the vibration section is not caused to vibrate, when the second count number of the biological information per the predetermined time period is 0.

15. A non-transitory computer-readable storage medium having stored thereon a program that is executable by a computer, the program being executable by the computer to perform functions comprising:

processing for detecting biological information of a human body by a biological information obtainment sensor;

processing for obtaining a first count number of the biological information per a predetermined time period at a first time point, and obtaining a second count number at a second time point which follows the first time point; and processing for causing a vibration section to vibrate with a first vibration in accordance with the biological information, when a difference obtained by subtracting the first count number from the second count number is larger than a positive first value at the second time point.

16. The non-transitory computer-readable storage medium according to claim 15, wherein the vibration section is caused to vibrate with a second vibration different from the first vibration in accordance with the biological information, when the difference of the biological information is smaller than a negative second value.

17. The non-transitory computer-readable storage medium according to claim 16, wherein the vibration section is caused to vibrate with a third vibration different from the first vibration and the second vibration in accordance with the biological information, when the difference of the biological information is in a range equal to or smaller than the positive first value and equal to or larger than the negative second value.

18. The non-transitory computer-readable storage medium according to claim 17, wherein the first vibration has an amplitude larger than an amplitude of the second vibration, and wherein the third vibration has a vibration period shorter than a vibration period of the first vibration and a vibration period of the second vibration.

19. The non-transitory computer-readable storage medium according to claim 18, wherein the vibration period of the first vibration is equal to the vibration period of the second vibration, and wherein the third vibration has an amplitude smaller than the amplitude of the first vibration and larger than the amplitude of the second vibration.

20. The non-transitory computer-readable storage medium according to claim 15, wherein the vibration section is not caused to vibrate, when the second count number of the biological information per the predetermined time period is 0.

* * * * *